United States Patent [19]

Skaborn et al.

[11] Patent Number: 5,895,630
[45] Date of Patent: Apr. 20, 1999

[54] SAFETY DEVICE FOR A PIPETTE ARM

[75] Inventors: Johan Skaborn; Björn Johansson; Kjell Årman, all of Uppsala; Leon Nordqvist, Malung, all of Sweden

[73] Assignee: Pharmacia & Upjohn AB, Uppsala, Sweden

[21] Appl. No.: 08/945,250

[22] PCT Filed: Apr. 24, 1996

[86] PCT No.: PCT/SE96/00537

§ 371 Date: Jan. 9, 1998

§ 102(e) Date: Jan. 9, 1998

[87] PCT Pub. No.: WO97/00450

PCT Pub. Date: Jan. 3, 1997

[30] Foreign Application Priority Data

Jun. 13, 1995 [SE] Sweden ................. 9502183

[51] Int. Cl.⁶ ............................................. G01N 35/10
[52] U.S. Cl. ............. 422/100; 422/63; 422/67; 422/107; 422/117; 73/864.24; 73/864.25
[58] Field of Search ............... 422/100, 63, 67, 422/105, 107, 117; 436/43, 50; 73/864.01, 864.23, 864.24, 864.25

[56] References Cited

U.S. PATENT DOCUMENTS

| | | |
|---|---|---|
| 4,037,476 | 7/1977 | McCrabb . |
| 4,276,260 | 6/1981 | Drbal et al. ................ 422/101 |
| 4,325,909 | 4/1982 | Coulter et al. ................ 422/63 |
| 5,027,075 | 6/1991 | Harding, Jr. ................ 324/662 |
| 5,334,349 | 8/1994 | Kelln et al. . |

FOREIGN PATENT DOCUMENTS

| | | |
|---|---|---|
| 0699910 | 3/1996 | European Pat. Off. . |
| 2131946 | 6/1984 | United Kingdom . |

*Primary Examiner*—Long V. Le
*Attorney, Agent, or Firm*—Dinsmore & Shohl LLP

[57] ABSTRACT

To interrupt the current to the drive motor (3) of a motor-driven arm (1) which carries a pipette (2) when something or someone unintentionally contacts the pipette (2) during its movement, the arm 1) has a lower, rigid part (5), and an upper, flexible part (6) which, at its one end, carries the pipette (2) and, at its other end, is rigidly connected to the lower arm part (5). The upper, flexible part (6) is in releasable contact with the lower, rigid part (5) at the end that carries the pipette (2), and is adapted to, at least partially, the released from that contact when something or someone unintentionally contacts the pipette (2) during its movement. A detecting means (9) is adapted to detect when the upper, flexible part (6), at least partially, is released from the contact with the lower, rigid part (5) and in response hereto cause a switch to brake the current to the drive motor (3) for the arm (1).

17 Claims, 1 Drawing Sheet

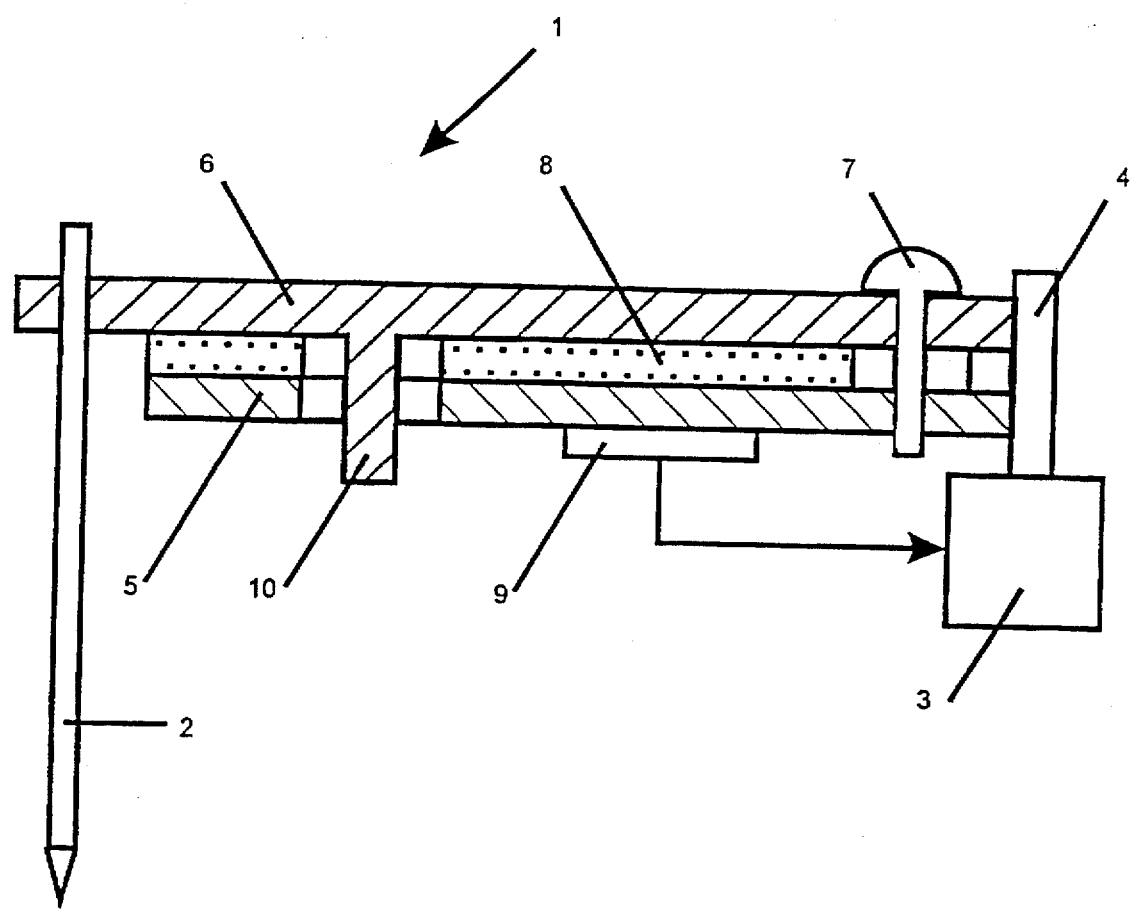

ND, 630

SAFETY DEVICE FOR A PIPETTE ARM

TECHNICAL FIELD

The invention relates to a safety device for a motor-driven arm which carries a pipette.

BACKGROUND OF THE INVENTION

In e.g. automatic medical analysis instruments where a pipette arm moves a pipette at great speed between a large number of test tubes, requirements have been set up stating that the pipette must not to cause personal injuries upon an unintentional contact with the pipette during operation.

One way of accomplishing this is to completely protect the area within which the pipette moves from contact by enclosing it in a protective housing.

Since there is a need of inserting or removing test tubes during operation of the pipette, the solution with a protective housing is not satisfactory.

BRIEF DISCLOSURE OF THE INVENTION

Therefore, the object of the invention is to bring about a safety device which automatically interrupts the operation of the pipette arm as soon as something or someone unintentionally contacts the pipette during its movement.

This is attained by means of the safety device mentioned in the introduction in that the arm has a lower, rigid part, and an upper, flexible part which, at its one end, carries the pipette and, at its other end, is rigidly connected to the lower arm part, that the upper, flexible part is in releasable contact with the lower, rigid part at the end that carries the pipette, and is adapted to, at least partially, be released from that contact when something or someone unintentionally contacts the pipette during its movement, and that detecting means are provided to detect when the upper, flexible part, at least partially, is released from the contact with the lower, rigid part and in response hereto cause a switch to break the current to the drive motor for the arm.

BRIEF DESCRIPTION OF THE DRAWING

The invention will be described more in detail below with reference to the appended drawing on which the single FIGURE schematically shows a longitudinal section of an embodiment of a pipette arm according to the invention.

DESCRIPTION OF PREFERRED EMBODIMENTS 1 generally denotes an arm which carries a pipette 2 and which, in the embodiment shown, is driven by a motor 3 on whose shaft 4 the pipette arm 1 is fixed in a manner not shown in any greater detail.

In the embodiment shown, the pipette 2 will thus be moved around the shaft 4. However, the invention is not restricted to the embodiment shown, but is applicable also to pipette arms which are driven in another manner than around a driving shaft.

In accordance with the invention, the arm 1 has a lower, rigid part 5, and an upper, flexible part 6, which, at its one end, carries the pipette 2 and, at its other end, is rigidly connected to the lower arm part 5 via e.g. a screw joint 7.

According to the invention, the upper, flexible arm part 6 is in releasable contact with the lower, rigid arm part 5 at the end that carries the pipette 2. To accomplish this releasable contact between the arm parts 5 and 6, in the embodiment shown on the drawing, a permanent magnet in the form of a magnetic sheet 8 is affixed to the lower, rigid arm part 5 which is made of non-magnetic material, while the upper, flexible part 6 is a leaf spring of a magnetic material.

Of course, the upper, flexible arm part 6 does not have to be of a magnetic material, but it can equally well be of a non-magnetic material and be provided with any suitable permanent magnet.

The purpose of the releasable contact between the arm parts 5 and 6, accomplished magnetically, is that these parts, at least partially, are to be separated from each other when any object or e.g. an operator's hand unintentionally contacts the pipette 2 during its movement. Thus, the magnet 8 is so dimensioned that its magnetic power is sufficient to keep the arm parts 5 and 6 mutually fixed during normal movements of the pipette 2.

According to the invention, detecting means are provided to detect when the upper, flexible arm part 6, at least partially, is released from the contact with the lower, rigid part 5.

In the embodiment shown on the drawing, the detecting means comprises a unit merely shown in the form of a block 9, which comprises a light source (not shown), e.g. a light emitting diode, which is adapted to illuminate a light reflective lug 10 on the upper, flexible arm part 6, which lug 10 extends below the lower, rigid arm part 5 through an opening in that arm part and in the magnetic sheet 8.

Light reflected by the lug 10 is detected by a light sensor (not shown) included in the unit 9, e.g. a photo diode, which is adapted to emit a signal on its output upon a change of the strength of the detected, reflected light in connection with a movement of the lug 10 when the upper arm part 6, at least partially, is released from the contact with the lower arm part 5 when something or someone unintentionally contacts the pipette 2 during its movement.

The output signal from the light sensor in the unit 9 is supplied to the control input of a switch (not shown) in the motor 3 to interrupt the current to the motor and hereby stop the movement of the shaft 4 and, thereby, the pipette arm 1.

Thanks to the flexibility of the upper arm part 6, very small changes of its position relative to the lower arm part 5 can be detected, and consequently, the time that it takes to stop the motor 3 will be very short. Hereby, the risk of damages that could be caused if the pipette arm continued its movement after that something or someone unintentionally contacted the pipette during its movement, is essentially eliminated.

We claim:

1. A motor-driven arm adapted for carrying a pipette, comprising:

an arm having a lower rigid part and an upper flexible part, one end of the upper flexible part being adapted to carry a pipette and being in releasable contact with the lower rigid part, and the other end of the upper flexible part being rigidly connected to the lower rigid part, the upper flexible part being at least partially releasable from contact with the lower rigid part when, during movement of the arm, something or someone unintentionally contacts the pipette carried by the upper flexible part;

a drive motor adapted for driving the arm; and a detecting means for detecting when the upper flexible part is at least partially released from contact with the lower rigid part and for causing a switch to interrupt current to the drive motor for the arm in response thereto.

2. A motor-driven arm according to claim 1, wherein the upper flexible part is a leaf spring.

3. A motor-driven arm according to claim 1, wherein the upper flexible part and the lower rigid part are magnetically interconnected to provide the releasable contact therebetween.

4. A motor-driven arm according to claim 2, wherein the upper flexible part and the lower rigid part are magnetically interconnected to provide the releasable contact therebetween.

5. A motor-driven arm according to claim 3, wherein the lower rigid part and the upper flexible part are magnetic.

6. A motor-driven arm according to claim 3, wherein the lower rigid part is formed of nonmagnetic material, the upper flexible part is formed of magnetic material and a permanent magnet is affixed to the lower rigid part.

7. A motor-driven arm according to claim 1, wherein the detecting means comprises a light source adapted to illuminate a light reflective lug provided on the upper flexible part, and a light sensor adapted to detect light reflected by the lug and to emit a signal upon a change of the strength of the reflected light in connection with a movement of the lug when the upper flexible part at least partially is released from contact with the lower rigid part, the emitted signal of the light sensor being connected to a control input of the switch to interrupt current to the drive motor for the arm.

8. A motor-driven arm according to claim 2, wherein the detecting means comprises a light source adapted to illuminate a light reflective lug provided on the upper flexible part, and a light sensor adapted to detect light reflected by the lug and to emit a signal upon a change of the strength of the reflected light in connection with a movement of the lug when the upper flexible part at least partially is released from contact with the lower rigid part, the emitted signal of the light sensor being connected to a control input of the switch to interrupt current to the drive motor for the arm.

9. A motor-driven arm according to claim 3, wherein the detecting means comprises a light source adapted to illuminate a light reflective lug provided on the upper flexible part, and a light sensor adapted to detect light reflected by the lug and to emit a signal upon a change of the strength of the reflected light in connection with a movement of the lug when the upper flexible part at least partially is released from contact with the lower rigid part, the emitted signal of the light sensor being connected to a control input of the switch to interrupt current to the drive motor for the arm.

10. A motor-driven arm according to claim 5, wherein the detecting means comprises a light source adapted to illuminate a light reflective lug provided on the upper flexible part, and a light sensor adapted to detect light reflected by the lug and to emit a signal upon a change of the strength of the reflected light in connection with a movement of the lug when the upper flexible part at least partially is released from contact with the lower rigid part, the emitted signal of the light sensor being connected to a control input of the switch to interrupt current to the drive motor for the arm.

11. A motor-driven arm according to claim 6, wherein the detecting means comprises a light source adapted to illuminate a light reflective lug provided on the upper flexible part, and a light sensor adapted to detect light reflected by the lug and to emit a signal upon a change of the strength of the reflected light in connection with a movement of the lug when the upper flexible part at least partially is released from contact with the lower rigid part, the emitted signal of the light sensor being connected to a control input of the switch to interrupt current to the drive motor for the arm.

12. A motor-driven arm according to claim 7, wherein the light source and the light sensor are provided on the lower rigid part and the lug extends from the upper flexible part through an opening in the lower rigid part.

13. A motor-driven arm according to claim 8, wherein the light source and the light sensor are provided on the lower rigid part and the lug extends from the upper flexible part through an opening in the lower rigid part.

14. A motor-driven arm according to claim 9, wherein the light source and the light sensor are provided on the lower rigid part and the lug extends from the upper flexible part through an opening in the lower rigid part.

15. A motor-driven arm according to claim 10, wherein the light source and the light sensor are provided on the lower rigid part and the lug extends from the upper flexible part through an opening in the lower rigid part.

16. A motor-driven arm according to claim 11, wherein the light source and the light sensor are provided on the lower rigid part and the lug extends from the upper flexible part through an opening in the lower rigid part.

17. A motor-driven arm adapted for carrying a pipette, comprising:

an arm having a lower rigid part and an upper flexible part, one end of the upper flexible part being adapted to carry a pipette and being in releasable contact with the lower rigid part, and the other end of the upper flexible part being rigidly connected to the lower rigid part, the upper flexible part being at least partially releasable from contact with the lower rigid part when, during movement of the arm, something or someone unintentionally contacts the pipette carried by the upper flexible part;

a drive motor adapted for driving the arm; and a detector adapted to detect when the upper flexible part is, at least partially, released from contact with the lower rigid part and adapted to cause a switch to interrupt current to the drive motor for the arm in response thereto.

* * * * *